United States Patent
Bhat et al.

(10) Patent No.: US 6,967,220 B2
(45) Date of Patent: Nov. 22, 2005

(54) PEPTIDE DEFORMYLASE INHIBITORS

(75) Inventors: Ajita Bhat, Collegeville, PA (US); Siegfried B. Christensen, IV, Collegeville, PA (US); James S. Frazee, King of Prussia, PA (US); Martha S. Head, Collegeville, PA (US); Jack D. Leber, King of Prussia, PA (US); Mei Li, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 62 days.

(21) Appl. No.: 10/473,060

(22) PCT Filed: Apr. 4, 2002

(86) PCT No.: PCT/US02/10648
§ 371 (c)(1),
(2), (4) Date: Sep. 29, 2003

(87) PCT Pub. No.: WO03/002522
PCT Pub. Date: Jan. 9, 2003

(65) Prior Publication Data
US 2004/0106795 A1 Jun. 3, 2004

Related U.S. Application Data
(60) Provisional application No. 60/281,611, filed on Apr. 5, 2001.

(51) Int. Cl.$^7$ .................. A61K 31/135; C07C 259/04; C07C 229/38

(52) U.S. Cl. ............... 514/645; 560/37; 562/621; 562/623

(58) Field of Search .................. 562/621, 623; 560/37; 514/645

(56) References Cited

PUBLICATIONS

Database CAPLUS on STN, Acc. No. 1974:59660, Ito et al. JP 48072138 A2 (Tanabe Seiyaku Co. Ltd.) Sep. 29, 1973, abstract.

Database CAPLUS on STN, Acc. No. 1975:39081, Miyagishima et al., Antibiotic YC–73 of Pseudomonas origin. IV. Further studies on synthese and antimicrobial activity of thioformin analogs. Chem. Pharm. Bull. (1974), 22(101);P. 2283–7 (abstract).

*Primary Examiner*—Brian Davis
(74) *Attorney, Agent, or Firm*—Laura K. Madden; Loretta J. Henderson; Mary E. McCarthy

(57) ABSTRACT

PDF inhibitors and novel methods for their use are provided.

6 Claims, 1 Drawing Sheet

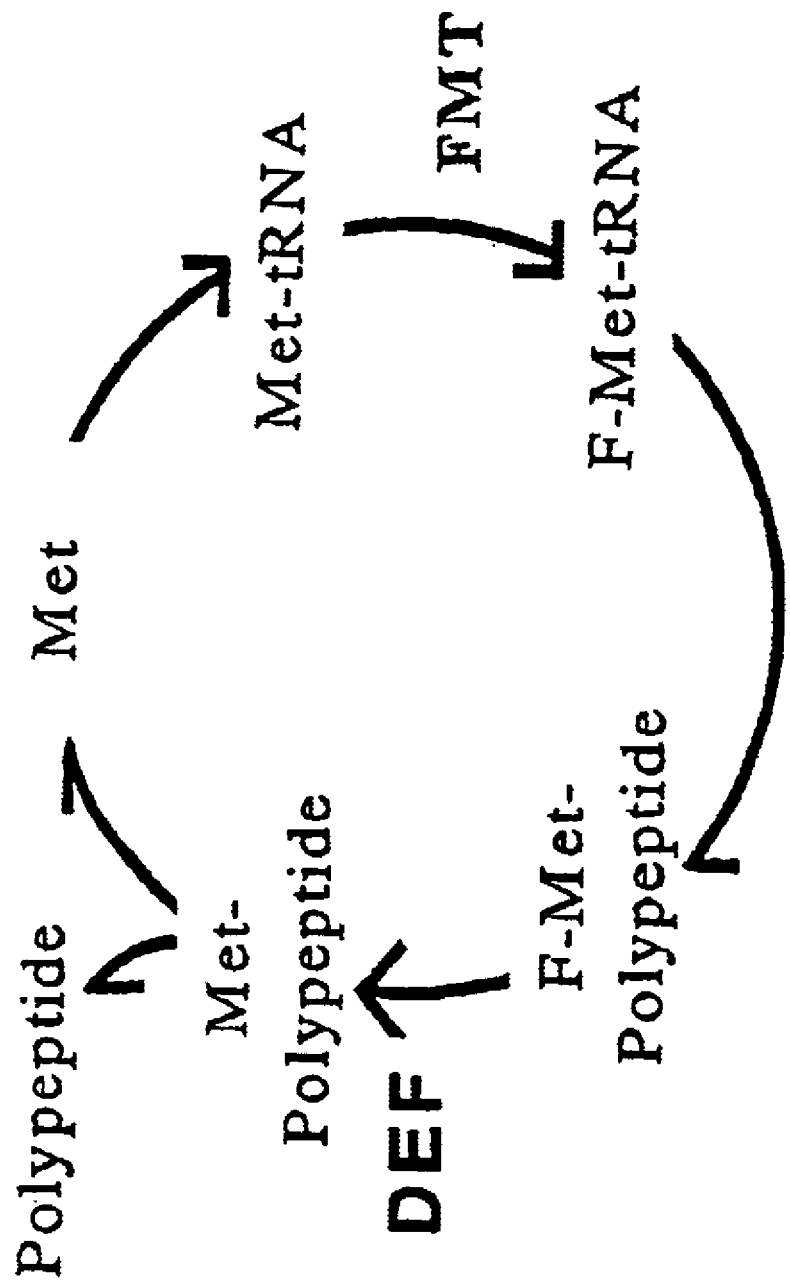
Figure 1. The methionine cycle.

PEPTIDE DEFORMYLASE INHIBITORS

This application claims the benefit of U.S. Provisional Application No. 60/281,611, filed 5 Apr. 2001.

FIELD OF THE INVENTION

The present invention relates to the use of novel anti-bacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

To date, polypeptide deformylase homologous genes have been found in bacteria, in chloroplast-containing plants, in mice and in human. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165–168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749–761, 1997).

PDF is recognized to be an attractive antibacterial target, as this enzyme has been demonstrated to be essential for bacterial growth in vitro (Mazel, D. et al., EMBO J. 13 (4), 914–923, 1994), is not believed to be involved in eukaryotic protein synthesis (Rajagopalan et al., J. Am. Chem. Soc. 119, 12418–12419, 1997), and is universally conserved in prokaryotes (Kozak, M., Microbiol. Rev. 47, 1–45, 1983). Therefore PDF inhibitors can potentially serve as broad spectrum antibacterial agents.

SUMMARY OF THE INVENTION

The present invention involves novel anti-bacterial compounds represented by Formula (I) hereinbelow and their use as PDF inhibitors.

The present invention further provides methods for inhibiting PDF in an animal, including humans, which comprises administering to a subject in need of treatment an effective amount of a compound of Formula (I) as indicated hereinbelow.

DETAILED DESCRIPTION OF THE INVENTION

The compounds useful in the present methods are selected from Formula (I) hereinbelow:

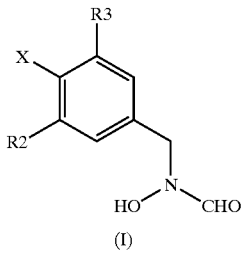

(I)

wherein:
X is selected from the group consisting of —C(O)OC$_{1-3}$ alkyl, —OR1, —NR1R6, —C(O)NR1R6, or —C(O)R6;
R1 is selected from the group consisting of hydrogen, C$_{1-6}$alkyl, unsubstituted or substituted by one or more moieties selected from the group consisting of halide, alcohol, ether, amine, amide, carboxylic acid, lactam, Ar, —C$_{1-2}$alkylAr, C$_{0-2}$alkylpiperidin-4-yl, substituted on nitrogen with R7, and C$_{0-2}$alkylpyrrolidin-3-yl, substituted on nitrogen with R7 or C$_{0-2}$ morpholine);
R6 is selected from the group consisting of hydrogen, C$_{1-6}$alkyl, unsubstituted or substituted by one or more moieties selected from the group consisting of halide, alcohol, ether, amine and amide;
or, R1 and R6 taken together may constitute a 5 or 6 member cyclic system which may contain an O or an optionally substituted N;
Ar is selected from the group consisting of phenyl, furyl, pyridyl, thienyl, thiazolyl, isothiazolyl, pyrazolyl, triazolyl, tetrazolyl, imidazolyl, benzofuranyl, indolyl, thiazolidinyl, isoxazolyl, oxadiazolyl, thiadiazolyl, pyrrolyl, and pyrimidyl, all of which may be unsubstituted or substituted by one or more R4 or R5 groups;
R2 is selected from the group consisting of I, Br, Cl, isopropyl and tert-butyl;
R3 is selected from the group consisting of H, I, Br, Cl, isopropyl, tert-butyl and Z-R8;
Z is selected from the group consisting of O, N, —NC(O), —C(O)N, —SO$_2$N, —CONHSO$_2$, —CONHNHCO and —CH$_2$;
R4 and R5 are independently selected from the group consisting of hydrogen, —OR9, —CN, F, Cl, Br, I, —CO$_2$H, —C(O)NR1R6, —NR6COR6, —NH$_2$, and —C$_{1-4}$alkyl which may be unsubstituted or substituted by one or more alcohol, amine, amide or carboxylic acid moieties;
R9 is H, —CH$_3$ or —CF3;
R7 is selected from the group consisting of hydrogen, —C$_{1-4}$ acyl and —C$_{1-4}$ alkoxycarbonyl;
R8 is selected from the group consisting of C$_{1-4}$ alkyl which may be unsubstituted or substituted by one or more alcohol, amine, amide, carboxylic acid, aryl or carbocycle.

As used herein, "alkyl" refers to an optionally substituted hydrocarbon group joined together by carbon-carbon bonds. The alkyl hydrocarbon group may be linear, branched or cyclic, saturated or unsaturated. Preferably, the group is linear. Preferably, the group is saturated. Preferred alkyl moieties are C$_{1-4}$ alkyl.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted. Preferred aryl moieties are phenyl, unsubstituted, monosubstituted, disubstituted or trisubstituted.

As used herein, the term "carbocycle" refers to a non-aromatic cyclic hydrocarbon radical having from three to seven carbon atoms. For carbocycles with five- to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

Preferred compounds useful in the present invention are selected from the group consisting of:
N-Hydroxy-N-(4-methoxy-3,5-dimethylbenzyl)formamide;
N-(3,5-Diisopropyl-4-methoxybenzyl)-N-hydroxyformamide;
Methyl 2,6-dichloro-4-(N-formyl-N-hydroxyaminomethyl) benzoate;
N-[3,5-Dichlorobenzyl]-N-hydroxyformamide;
N-[3,5-Dichloro-4-methoxybenzyl]-N-hydroxyformamide;
N-Hydroxy-N-(4-amino-3,5-dichlorobenzyl)formamide;
N-[3,5-Dichloro-4-(2-thiophen-2-ylethoxy)benzyl]-N-hydroxyformamide;
N-[3,5-Dichloro-4-(2-hydroxyethoxy)benzyl]-N-hydroxyformamide;
N-[3,5-Dichloro-4-(pyridin-4-ylmethoxy)-benzyl]-N-hydroxy-formamide;
N-[3,5-Dichloro-4-((S)-1-methyl-2,5-dioxo-pyrrolidin-3-yloxy)-benzyl]-N-hydroxy-formamide;
2-Butoxy-3-chloro-N-(2,3-dihydroxypropyl)-5-[(formylhydroxyamino)methyl]-benzamide;
N-{3,5-Dichloro-4-[2-(2-oxo-pyrrolidin-1-yl)-ethoxy]-benzyl}-N-hydroxy-formamide;
2-Butoxy-3-chloro-5-[(formyl-hydroxy-amino)-methyl]-benzoic acid methyl ester;
N-[3,5-Dichloro-4-(1-ethyl-butoxy)-benzyl]-N-hydroxy-foramide;
N-hydroxy-N-(3-iodo-5-methoxy-4-phenoxy-benzyl)-formamide;
N-(4-butoxy-3-iodo-5-methoxy-benzyl)-N-hydroxy-formamide;
N-(4-cyclohexyloxy-3,5-dichloro-benzyl)-N-hydroxy-formamide;
N-(2-Acetylaminoethyl)-2-butoxy-3-chloro-5-[(formylhydroxyamino)methyl]benzamide;
N-(4-butoxyl-3-chloro-5-hydroxy-benzyl)-N-hydroxy-formamide;
N-hydroxy-N-[3-iodo-5-methoxy-4-(2-methoxy-ethoxy)-benzyl]-formamide;
N-[3-Chloro-4-(3,4-dichloro-phenoxy)-5-methoxy-benzyl]-N-hydroxy-formamide;
N-[4-butoxy-2,3-dichloro-5-methoxy-benzyl]-N-hydroxy-formamide;
N-{2-Butoxy-5-[(formyl-hydroxy-amino)-methyl]-3-iodo-phenyl}-acetamide;
2-{2-Butoxy-5-[(formyl-hydroxy-amino)-methyl]-3-iodo-phenoxy}-N-methyl-acetamide and
N-(3-Chloro-5-methoxy-4-phenoxybenzyl)-N-hydroxyformamide.

More preferred compounds useful in the present invention are selected from the group consisting of:
N-Hydroxy-N-[4-(4-hydroxyphenoxy)-3,5-diiodobenzyl] formamide;
N-[3,5-Dichloro-4-(4-methoxyphenoxy)benzyl]-N-hydroxyformamide;
N-(4-Butoxy-3,5-dichlorobenzyl)-N-hydroxyformamide;
N-(3-Chloro-5-methoxy-4-phenoxybenzyl)-N-hydroxyformamide;
N-(4-butoxy-3-chloro-5-methoxybenzyl)-N-hydroxy-formamide;
2-{2-Butoxy-3-chloro-5-[(formylhydroxyamino)methyl] phenoxy}-N-methyl acetamide and
N-(4-Butoxy-3-iodo-5-methylamino-benzyl)-N-hydroxy-formamide.

Also included in the present invention are pharmaceutically acceptable salts and complexes. The compounds of the present invention may contain one or more asymmetric carbon atoms and may exist in racemic and optically active forms. All of these compounds and diastereomers are contemplated to be within the scope of the present invention.

The compounds and processes of the present invention will be better understood in connection with the following synthetic schemes, which are merely illustrative of the methods by which the compounds of the invention may be prepared and are not intended to limit the scope of the invention as defined in the appended claims.

Compounds of the formula 1 in which R1 is alkoxy are prepared by the methods described in Scheme 1.

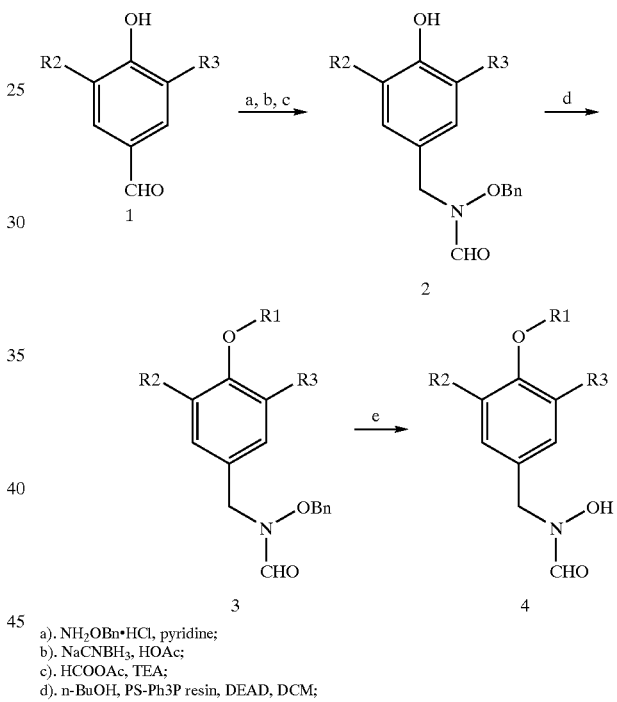

a). NH$_2$OBn•HCl, pyridine;
b). NaCNBH$_3$, HOAc;
c). HCOOAc, TEA;
d). n-BuOH, PS-Ph3P resin, DEAD, DCM;
e). H$_2$, 10% Pd/C Protected N-formyl-N-hydroxyl amines, such as 2-Scheme 1, may be prepared by reductive amination of the appropriately substituted hydroxy benzaldehyde, such as 1-Scheme 1, using a protected hydroxyl amine, such as O-benzylamine, with a reducing reagent, such as sodium cyanoborohydride, followed by N-formylation using formic acid with acetic anhydride and a base such as triethylamine. Alkylation of 2-Scheme 1 is accomplished using Mitsunobu conditions and an alcohol, such as butanol, to afford ethers of the type 3-Scheme 1. Deprotection using a catalyst, such as palladium on carbon, under an atmosphere of hydrogen yields N-formyl hydroxyl amines of the type 4-Scheme 1.

Compounds of the formula 1 in which R1 is aryloxy are prepared by the methods described in Scheme 2.

Scheme 2

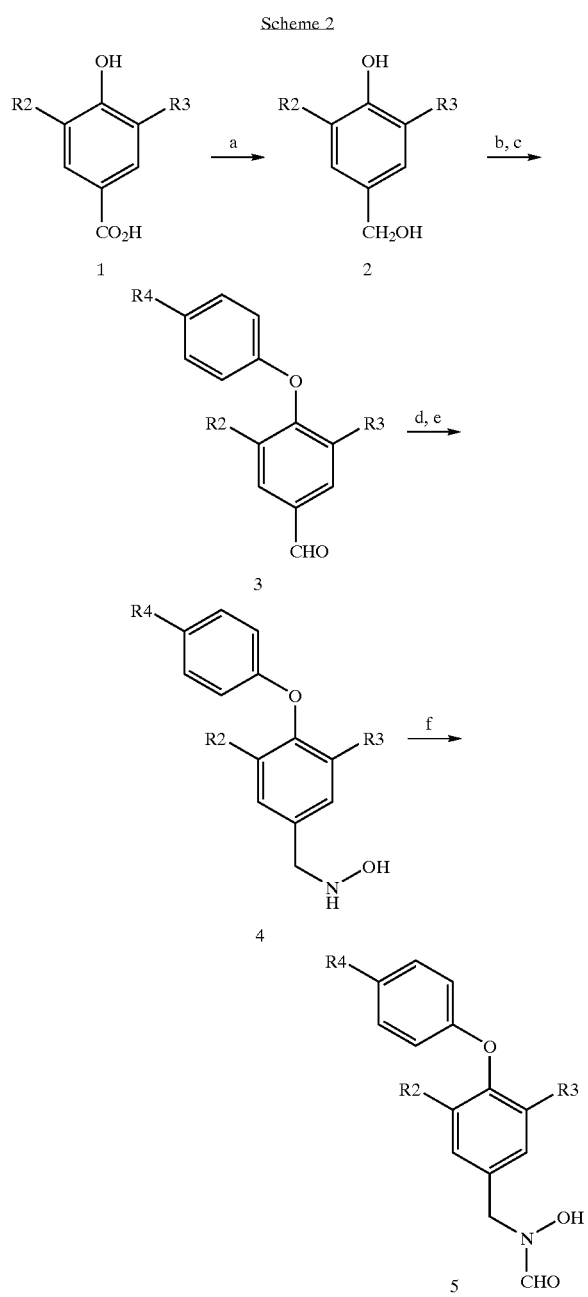

a). B₂H₆, THF;
b). PhB(OH)₂, Cu(OAc)₂, 4-A sieves, CH₂Cl₂, pyridine, TEA;
c). PCC, DCM;
d). NH₂OH•HCl, pyridine;
e). NaCNBH₃, HOAc;
f). HCOOAc, TEA The benzyl alcohol 2-Scheme 2 may be prepared by reduction of the appropriately substituted hydroxybenzoic acid, such as 1-Scheme 2, using a reducing agent, such as diborane in a solvent such as THF. Treatment of a phenol, such as 2-Scheme 2 with an aryl boronate, such as benzene boronic acid with copper acetate, pyridine, triethyl amine and 4 A sieves will provide a biaryl ether, such as 3-Scheme 2. Reductive amination using hydroxyl amine with a reducing reagent, such as sodium cyanoborohydride, followed by N-formylation using formic acid with acetic anhydride and a base such as triethylamine in a solvent such as dichloromethane yields N-formyl-N-hydroxyl amines such as 5-Scheme 2.

Alternatively, the N-formal hydroxylamine can be prepared by the method described in scheme 3.

Scheme 3

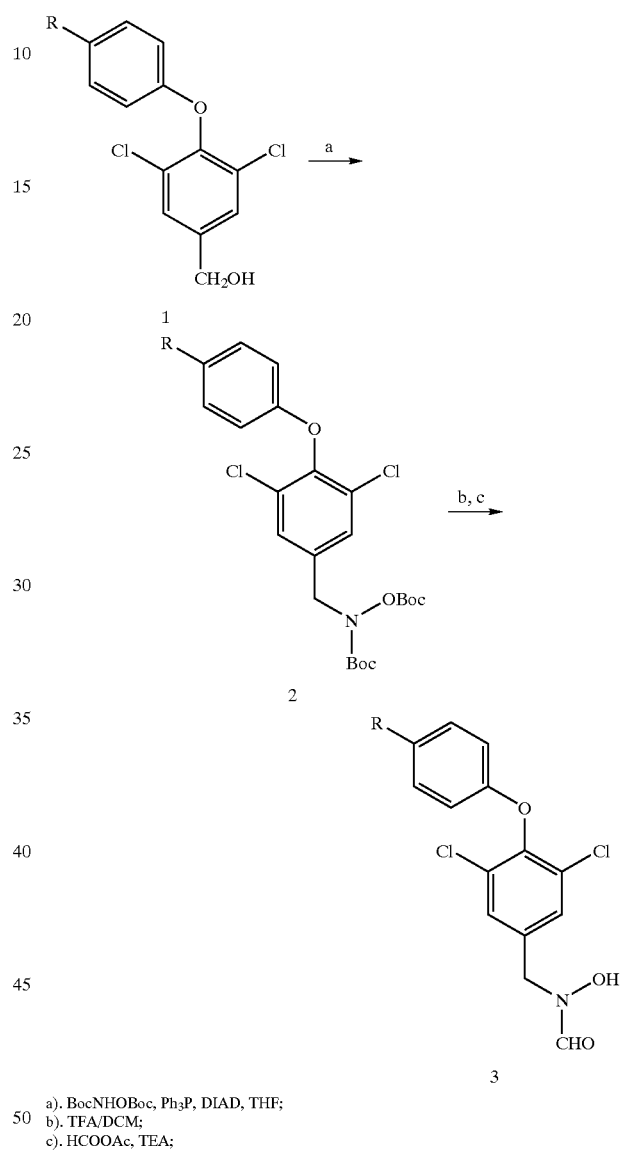

a). BocNHOBoc, Ph₃P, DIAD, THF;
b). TFA/DCM;
c). HCOOAc, TEA;

A bis-Boc protected N-hydroxyl amine such as 2-Scheme 3 may be prepared by Mitsunobu reaction on an appropriately functionalized benzyl alcohol such as 1-Scheme 3 using reagents such as triphenylphosphine, diisopropyl azodicarboxylate, and tert-butyl N-(tert-butoxycarbonyloxy) carbamate in a solvent such as THF. Compounds such as 2-Scheme 1 may be deprotected by treatment with an acid, such as TFA, in a solvent such as dichloromethane. N-formylation using formic acid with acetic anhydride and a base such as triethylamine in a solvent such as dichloromethane yields N-formyl-N-hydroxyl amines such as 5-Scheme 2. Compounds of the formula 1 in which X=O and R3 is alkyloxy are prepared by the methods described in Scheme 4.

Scheme 4

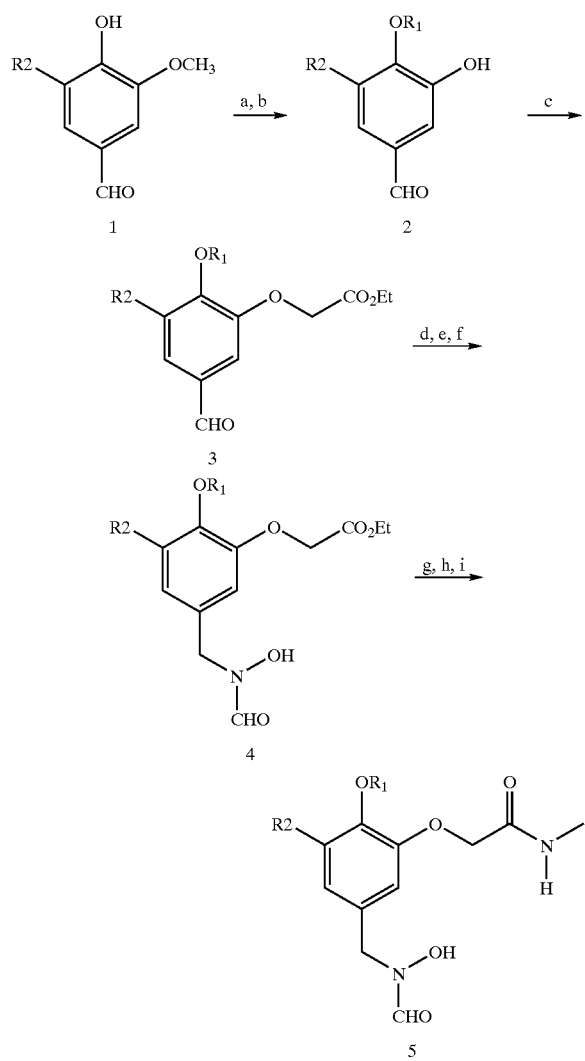

a). BBr₃, CH₂Cl₂;
b). ROH, Ph₃P, DEAD, THF;
c). ethyl bromoacetate, NaH, DMF;
d). NH₂OH HCl, pyridine;
e). NaCNBH₃, HOAc;
f). HOAc, HCO₂H, TEA;
g). NaOH, H₂O, CH₃OH;
h). ClCO₂Et, TEA, THF;
i). NH₂CH₃

A 4-alkoxybezaldehyde such as 4-butoxy-3-chloro-5-hydroxy benzaldehyde (2 scheme 4) can be prepared by demethylation of an appropriately substituted benzaldehyde such as 1 scheme 4 followed by a Mitsunobu reaction using an alcohol such as n-butanol with triphenylphosphine and diethyldicarboxylate. This can be alkylated with an alkylhalide such as ethyl bromoacetate and a base such as sodium hydride in a suitable solvent such as DMF. The aldehyde can be converted to a formylhydroxyl amine using methods described in scheme 2. The ester can be converted to an amide by saponification using a base such as sodium hydroxide in a suitable solvent mixture such as methanol and water. The resulting acid can be treated with ethylchloroformate and TEA to form a mixed anhydride which can then be treated with an amine such as methyl amine to form the amide 5 scheme 4.

The foregoing may be better understood by reference to the following examples which illustrate the methods by which the compounds of the invention may be prepared and are not intended to limit the scope of the invention as defined in the appended claims.

EXAMPLE 1

Preparation of N-hydroxy-N-[4-(4-hydroxyphenoxy)-3,5-diiodobenzyl]formamide a) 4-(4-Hydroxymethyl-2,6-diiodo-phenoxy)phenol To a solution of 4-(4-hydroxy-phenoxy)-3,5-diiodobenzoic acid (400 mg, 0.828 mmol) in THF (6.0 ml) under argon was added borane-THF complex (3.31 mmol, 3.31 ml of 1M solution in THF) dropwise. After addition, the reaction mixture was heated at 60° C. for 3 h, then quenched with water and extracted with ethyl acetate three times. The organic extract was washed with water, then brine, dried (sodium sulfate) and concentrated in vacuo to afford the title compound (321 mg, 83%) as a white solid. $^1$H NMR (400 MHz, CDCl$_3$) δ 7.79 (s, 2H), 6.67 (d, j=8.8 Hz, 2H), 6.55 (d, j=8.8 Hz, 2H), 4.55 (s, 2H) MS: (M$^{+1}$-H$_2$O)=451 b) tert-Butyl N-(tert-butoxycarbonyloxy)-N-[3,5-diiodo-4-(4-hydroxy phenoxy) benzyl]carbamate To an ice-cold solution 4-(4-hydroxymethyl-2,6-diiodophenoxy)phenol (239 mg, 0.51 mmol) in THF (2 ml) with tert-butyl N-(tert-butoxycarbonyloxy) carbamate (595 mg, 2.55 mmol), and triphenylphosphine (160 mg, 0.61 mmol) was added diisopropyl azodicarboxylate (120 ul, 0.61 mmol). The reaction was stirred 10 min. then all volatiles were removed in vacuo. The residue was chromatographed on silica to afford the title compound (150 mg, 43%) as a white solid. $^1$H NMR (400 MHz, CDCl$_3$) δ 7.82 (s, 2H), 6.74 (d, j=8.8 Hz, 2H), 6.66 (d, j=8.8 Hz, 2H), 4.68 (s, 2H), 1.51 (s, 18H).

c) N-Hydroxy-N-[4-(4-hydroxyphenoxy)-3,5-diiodobenzyl]formamide

A solution containing tert-butyl N-(tert-butoxycarbonyloxy)-N-[3,5-diiodo-4-(4-hydroxyphenoxy) benzyl]carbamate (150 mg, 0.21 mmol) in 4 ml of 30% TFA in CH$_2$Cl$_2$ was stirred for 2 h and then evaporated to dryness to afford 4-(4-hydroxyaminomethyl-2,6-diiodophenoxy) phenol (M$^{+1}$=484). This residue was then treated with triethylamine (0.5 ml) and the mixed anhydride (0.5 ml) [made from formic acid and acetic anhydride (1:2 v/v) at 50° C. for 1 h] in 2 ml of CH$_2$Cl$_2$ for 0.5 h. All volatiles were removed and the residue dissolved in methanol then treated with 10% NaOH for 0.5 h. This was diluted with ethyl acetate and water and adjusted to pH of 6. The layers were separated and the organic extract was evaporated in vacuo. Purification by preparative HPLC afforded the title compound (27 mg, 25%) as an off white solid. $^1$H NMR (400 MHz, CD$_3$OD): δ 8.38, 8.18* (s, 1H); 7.89*, 7.86 (s, 2H); 6.69 (d, j=8.8 Hz, 2H); 6.55 (d, j=8.8 Hz, 2H),; 4.67, 4.63* (s, 2H). M$^{+1}$=512. *: minor rotamer

EXAMPLE 2

Preparation of N-[3,5-dichloro-4-(4-methoxyphenoxy)benzyl]-N-hydroxyformamide a) 2,6-Dichloro-4-hydroxymethylphenol To a solution of 3,5-dichloro-4-hydroxybenzoic acid (4.0 g, 19.3 mmol) in THF (60 ml) under argon was added borane-THF complex (39.0 mmol, 39.0 ml of 1 M solution in THF) dropwise. After addition, the reaction mixture was heated at 60° C. for 6 h, then quenched with water and extracted with ethyl acetate three times. The organic extract was washed with water, then brine, dried (sodium sulfate) and concentrated in vacuo to afford the title compound (3.7 g, 99%) as white solid. $^1$H NMR (400 MHz, CDCl$_3$) δ 7.28 (s, 2H), 5.83 (s, 1H), 4.59 (s, 2H), MS: (M$^{+1}$-H$_2$O)=175 b) 3,5-Dichloro-4-(4-methoxyphenoxy)benzyl Alcohol

To a flask containing 24 ml of dichloromethane was added 4 Å sieves (2.97 g, activated at 500° C. for 8 h), 4-methoxyphenylboronic acid (1.84 g, 12.0 mmol), 2,6-dichloro-4-hydroxymethylphenol (465 mg, 2.41 mmol), copper (II) acetate (438 mg, 2.41 mmol), pyridine (0.97 ml, 12.0 mmol) and triethylamine (1.67 ml, 12.0 mmol). The reaction flask was fitted with a drying tube and stirred overnight. Filtration through celite and removal of volatiles in vacuo followed by column chromatography (silica, 30% ethyl acetate in hexane) provided the title compound as light brown oil (323 mg, 44%). $^1$H NMR (400 MHz, CDCl$_3$) δ 7.39 (s, 2H), 6.82 (d, j=7.2 Hz, 2H), 6.77 (d, j=7.2 Hz, 2H), 4.69 (s, 2H), 3.76 (s, 3H).

c) 3,5-Dichloro-4-(4-methoxyphenoxy)benzaldehyde

To an ice-cold solution of 3,5-dichloro-4-phenoxybenzyl alcohol (200 mg, 0.67 mmol) in 6.7 ml of dichloromethane with 4 Å sieves was added a mixture of pyridinium chlorochromate (317 mg, 1.47 mmol) and celite (317 mg). The reaction mixture was brought to room temperature and stirred for 1 h then diluted with diethyl ether and passed through a column of florisil. Removal of volatiles in vacuo afforded the title compound as a solid (175 mg, 88%). $^1$H NMR (400 MHz, CDCl$_3$) δ 9.93 (s, 1H), 7.91 (s, 2H), 6.83 (d, j=6.8 Hz, 2H), 6.77 (d, j=6.8 Hz, 2H), 3.77 (s, 3H). $M^{+1}$=297.

d) N-[3,5-Dichloro-4-(4-methoxyphenoxy)benzyl]-N-hydroxy-formamide

A solution of 3,5-dichloro-4-(4-methoxyphenoxy)benzaldehyde (170 mg, 0.572 mmol) and hydroxylamine hydrochloride (48 mg, 0.687 mmol) in 1 ml of pyridine was stirred for 1 h then all volatiles were removed in vacuo. The resulting imine intermediate was treated with sodium cyanoborohydride (122 mg, 1.944 mmol) in 2 ml of glacial acetic acid for 5 h. The reaction mixture was then quenched with water and neutralized with sodium bicarbonate powder, extracted with ethyl acetate and dried (sodium sulfate). The resulting 3,5-dichloro-N-hydroxy-4-(4-methoxyphenoxy)benzyl amine was converted to the title compound using the method described in example 1c (50 mg, 26%) as an off-white solid. $^1$H NMR (400 MHz, CDCl3) δ 8.06 (s, 1H), 7.34 (s, 2H), 6.82 (d, j=8.8 Hz, 2H), 6.76 (d, j=8.8 Hz, 2H), 4.64 (s, 2H), 3.76 (s, 3H). $M^{+1}$=342.

EXAMPLE 3

Preparation of N-(4-butoxy-3,5-dichlorobenzyl)-N-hydroxyformamide a) N-benzyloxy-N-(3,5-dichloro-4-hydroxybenzyl)formamide A solution of 3,5-dichloro-4-hydroxybenzaldehyde (2.00 g, 10.5 mmol) and O-benzylhydroxylamine hydrochloride (1.84 g, 11.55 mmol) in 5 ml of pyridine was stirred for 2 h. All volatiles were removed in vacuo and the resulting imine intermediate was treated with sodium cyanoborohydride (1.98 g, 31.5 mmol) in 10 ml of glacial acetic acid for 4 h. The reaction mixture was quenched with water and neutralized with sodium bicarbonate powder, extracted with ethyl acetate and dried (sodium sulfate). Removal of all volatiles in vacuo afforded the crude 4-(Benzyloxyamino-methyl)-2,6-dichlorophenol (4.02 g) as a light yellow oil ($M^{+1}$=298). This was converted to the title compound using the method described in example 1c (2.01 g, 59%) as a thick colorless oil. $^1$H NMR (400 MHz, CDCl3) δ 8.25 (s, 1H), 7.38 (m, 3H), 7.28 (m, 2H), 7.19 (s, 2H), 5.97 (s, 1H), 4.78 (s, 2H), 4.55 (s, 2H). $M^{+1}$=326.

b) N-Benzyloxy-N-(4-butoxy-3,5-dichlorobenzyl)formamide

To a solution of N-benzyloxy-N-(3,5-dichloro-4-hydroxybenzyl)formamide in methylene chloride (5 ml) was added n-butanol (110 ul, 1.2 mmol) and Polymer-bound triphenyl phosphine resin (500 mg, 1,2 mmol/g, 0.6 mmol). The reaction mixture was stirred for 0.5 h at room temperature then cooled to 0° C. A solution of DEAD (0.6 mmol, 95 ul) in methylene chloride (1 ml) was added and the reaction mixture stirred at room temperature for 16 h. The resin was filtered and washed with methylene chloride three times and the filtrate was evaporated to afford the crude N-benzyloxy-N-(4-butoxy-3,5-dichlorobenzyl)formamide as a white solid. $^1$H NMR (400 MHz, CDCl3) δ 8.25 (s, 1H), 7.38 (m, 3H), 7.28 (m, 2H), 7.19 (s, 2H), 4.78 (s, 2H), 4.57 (s, 2H), 4.00 (t, j=6.4 Hz, 2H), 1.82 (quint, j=7.6 Hz, 2H), 1.55(sext, j=7.6 Hz, 2H), 0.98 (t, j=7.6 Hz, 3H). $M^{+1}$=382 c) N-(4-Butoxy-3,5-dichlorobenzyl)-N-hydroxyformamide

To a solution of the crude N-benzyloxy-N-(4-butoxy-3,5-dichlorobenzyl)formamide in 5 ml of methanol was added 100 mg of 10% palladium on carbon. This was stirred under a hydrogen atmosphere for 50 min. Filtration and removal of volatiles in vacuo then purification by preparative HPLC afforded the title compound (71 mg, 41%) as an off-white solid. $^1$H NMR (400 MHz, CD$_3$OD) δ 8.36, 8.20* (s, 1H); 7.37*, 7.33 (s, 2H); 4.64, 4.61* (s, 2H); 4.01 (t, j=6.4 Hz, 2H), 1.80 (quint, j=7.6 Hz, 2H), 1.57 (sext, j=7.6 Hz, 2H), 1.00 (t, j=7.2 Hz, 3H). $M^{+1}$=292.*: minor rotamer

EXAMPLE 4

Preparation of N-(3-Chloro-5-methoxy-4-phenoxybenzyl)-N-hydroxyformamide a) 3-Chloro-5-methoxy-4-phenoxybenzaldehyde To a flask containing dichloromethane (58 ml) was added powdered 4 Å sieves (3.37 g, activated at 500° C. for 8 h), phenylboronic acid (3.53 g, 28.95 mmol), 3-chloro-4-hydroxy-5-methoxybenzaldehyde (1.08 g, 5.79 mmol), copper (II) acetate (1.05 g, 5.79 mmol), pyridine (2.33 ml, 28.95 mmol) and triethylamine (4.0 ml, 28.95 mmol). The reaction flask was fitted with a drying tube and stirred overnight at room temperature. Filtration through celite and removal of volatiles in vacuo followed by column chromatography (silica, 10% ethyl acetate in hexane) provided the title compound as a yellow solid (540 mg, 35%). $^1$H NMR (400 MHz, CDCl$_3$) δ 9.93 (s, 1H), 7.60 (s, 1H), 7.44 (s, 1H), 7.28 (t, j=8.0 Hz, 2H), 7.05 (t, j=7.2 Hz, 1H), 6.83 (d, j=8.4 Hz, 2H), 3.84 (s, 3H). $M^{+1}$=263 b) N-(3-Chloro-5-methoxy-4-phenoxy-benzyl)-N-hydroxy formamide

3-Chloro-5-methoxy-4-phenoxybenzaldehyde was converted to the title compound using the methods described in example 2d, (37 mg) as an off-white solid. $^1$H NMR (400 MHz, CD$_3$OD) δ 8.40, 8.21* (s, 1H), 7.24 (t, j=7.2 Hz, 2H), 7.10, 7.07* (s, 1H), 7.06*, 7.03 (s, 1H), 6.97 (t, j=7.2 Hz, 1H), 6.75 (d, j=8.0 Hz, 2H), 4.72, 4.68* (s, 2H), 3.77*, 3.75 (s, 3H). $M^{+1}$=308.

EXAMPLE 5

Preparation of 2-{2-butoxy-3-chloro-5-[(formylhydroxyamino)methyl]-phenoxy}-N-hydroxyformamide a) 3-Chloro-4,5-dihydroxybenzaldehyde To a solution of 3-Chloro-4-hydroxy-5-methoxybenzaldehyde (1.0 g, 5.4 mmol) in dichloromethane (150 ml) stirred at −78° C. was added dropwise a solution of boron tribromide in dichloromethane (5.4 ml of 1M solution, 5.4 mmol). Upon completion of the addition, the resulting solution was stirred 18 h at room temperature. The reaction was quenched by addition of methanol then evaporated twice from methanol and the residue purified by reversed-phase preparative HPLC to afford the title compound (0.66 g, 72%). $^1$H NMR (400 MHz, CD$_3$OD) δ 9.69 (s, 1H), 7.42 (s, 1H), 7.25 (s, 1H). M$^{+1}$=173.

b) 4-Butoxy-3-chloro-5-hydroxybenzaldehyde

A solution consisting of 3-chloro-4,5-dihydroxybenzaldehyde (3.0 g, 17.4 mmol), n-butanol (1.42 g, 19.1 mmol), triphenylphosphine (5.02 g, 19.4 mmol), and diethylazodicarboxylate (3.32 g, 19.1 mmol) in THF (60 ml) was stirred at room temperature for 24 h. All volatiles were removed in-vacuo and the residue purified by preparative HPLC to afford the title compound (2.7 g, 68%). $^1$H NMR (400 MHz, CDCl$_3$) δ 9.84 (s, 1H), 7.46 (d, j=1.8 Hz, 1H), 7.38 (d, j=1.8 Hz, 1H), 5.91 (s, 1H), 4.18 (t, j=6.7 Hz, 2H), 1.83 (m, 2H), 1.51 (m, 2H), 1.00 (t, j=7.4). M$^{+1}$=299.

c) (2-Butoxy-3-chloro-5-formylphenoxy)acetic acid ethyl ester

Sodium hydride (84 mg 60% in mineral oil, 2.09 mmol) was added in portions to a solution of 4-butoxy-3-chloro-5-hydroxybenzaldehyde (400 mg, 1.74 mmol) in DMF (5 ml). The resultant mixture was stirred at room temperature for 10 min then ethyl bromoacetate (583 mg, 3.5 mmol) was added slowly. After 1.5 h at room temperature, HPLC indicated complete reaction. The mixture was partitioned between ethyl acetate and water, the organic solution was washed with water then brine and dried with magnesium sulfate. Removal of all volatiles in-vacuo afforded the title compound (100% crude yield). $^1$H NMR (400 MHz, CDCl$_3$) δ 9.82 (s, 1H), 7.55 (d, j=1.8 Hz, 1H), 7.25 (d, j=1.8 Hz, 1H), 4.73 (s, 2H), 4.21–4.30 (m, 4H) 1.79–1.60 (m, 2H), 1.52–1.60 (m, 2H), 1.31 (t, j=7.1 Hz, 3H), 0.98 (t, j=7.1 Hz, 3H). M$^{+1}$=315.

d) 2-Butoxy-3-chloro-5-[(formylhydroxyamino)methyl]phenoxyacetic acid ethyl ester 2-Butoxy-3-chloro-5-formylphenoxyacetic acid ethyl ester was converted to the title compound using the methods described in example 2d. $^1$H NMR (400 MHz, CDCl$_3$) δ 8.38* 8.00 (s, 1H), 7.01* 6.98 (s, 1H), 6.70 (s, 1H), 4.68 (s, 2H), 4.60* 4.54 (s, 2H), 4.25 (q, j=7.1 Hz, 2H), 4.07 (t, j=6.6 Hz, 2H) 1.75–1.82 (m, 2H), 1.50–1.56 (m, 2H), 1.29 (t, j=7.1 Hz, 3H), 0.97 (t, j=7.3 Hz, 3H). M$^{+1}$=360.

* signals due to minor rotamer e) 2-Butoxy-3-chloro-5-[(formylhydroxyamino)methyl]phenoxyacetic acid A solution of 2-butoxy-3-chloro-5-[(formylhydroxyamino)methyl]phenoxyacetic acid ethyl ester (0.45 mmol crude) in methanol (5 ml) with 10% aqueous NaOH solution (0.5 ml) was stirred for 1 h. To the resulting solution was added ethyl acetate (20 ml) and water (20 ml). The pH was brought to 6 with 3 N HCl and the layers separated. The organic extract was dried with magnesium sulfate and all volatiles removed. The residue was purified by preparative HPLC to afford the title compound (29 mg, 20% for four steps). $^1$H NMR (400 MHz, CD$_3$OD) δ 8.37* 8.18 (s, 1H), 7.04* 7.02 (s, 1H), 6.90* 6.88 (s, 1H), 4.75* 4.74 (s, 2H), 4.63* 4.10 (m, 2H), 1.76–1.79 (m, 2H), 1.53–1.59 (m, 2H), 0.98–1.02 (m, 3H). M$^{+1}$=332.

* signals due to rotamer f) 2-{2-Butoxy-3-chloro-5-[(formylhydroxyamino)methyl]-phenoxy}-N-hydroxyformamide To a solution of 2-butoxy-3-chloro-5-[(formylhydroxyamino)methyl]phenoxyacetic acid (crude 0.5 mmol) in THF (4 ml) with TEA (0.167 ml, 1.2 mmol) was added ethyl chloroformate (0.115 ml, 1.2 mmol). This was stirred 15 min then methyl amine (0.21 ml of 40% aqueous solution) was added and stirring continued for an additional 30 min. The mixture was partitioned between ethyl acetate and water aqueous layer adjusted to pH 5 with 1 N HCl). The organic extract was dried with magnesium sulfate and all volatiles removed in vacuo. Purification by preparative HPLC afforded the title compound (10 mg). $^1$H NMR (400 MHz, CD$_3$OD) δ 8.38* 8.18 (s, 1H), 7.11* 7.08 (s, 1H), 6.98* 6.95 (s, 1H), 4.59–4.65 (m, 4H), 2.84 (s, 3H), 1.76–1.80 (m, 2H), 1.55–1.60 (m, 2H), 1.01 (t, j=7.4 Hz, 3H). M$^{+1}$=345.

* signals due to rotamer

EXAMPLE 6

Preparation of N-(4-butoxy-3-iodo-5-methylaminobenzyl)-N-hydroxyformamide a) 4-Butoxy-3-iodo-5-nitrobenzaldehyde To a slurry of 4-hydroxy-3-iodo-5-nitrobenzaldehyde (3.16 g, 10.7 mmol) in THF (100 ml) was added n-butanol (1.94 ml, 21.5 mmol), triphenyl phosphine (3.10 g, 11.8 mmol) and diethylazodicarboxylate (1.85 ml, 11.8 mmol). The mixture was stirred 18 h then filtered and all volatiles removed the residue was chromatographed on silica to afford the title compound (2.74 g, 73%).). $^1$H NMR (400 MHz, CDCl$_3$) δ 9.94 (s, 1H), 8.54 (d, j=2.0 Hz, 1H), 8.28 (d, j=2.0 Hz, 1H), 4.18 (t, j=6.5, 2H), 1.86–1.94 (m, 2H), 1.52–1.61 (m, 2H), 1.01 (t, j=7.1 Hz, 3H). M$^{+1}$=350.

b) 5-Amino-4-butoxy-3-iodobenzaldehyde

To a solution of 4-butoxy-3-iodo-5-nitrobenzaldehyde (3.35 g, 9.6 mmol) in ethanol (60 ml) with water (3 ml) was added SnCl$_2$ (9.1 g, 48 mmol). This was refluxed 2 h then all volatiles were removed. The residue was dissolved in EtOAc and the solution was washed twice with 10% aqueous NaOH solution then three times with water then brine. The organic solution was dried with magnesium sulfate, all volatiles removed and the resulting product (2.66 g, 83%) used without purification. $^1$H NMR (400 MHz, CDCl$_3$) δ 9.78 (s, 1H), 7.65 (d, j=1.9 Hz, 1H), 7.21 (d, j=2.0 Hz, 1H), 3.98 (t, j=6.5 Hz, 2H), 1.84–2.01 (m, 2H), 1.54–1.61 (m, 2H), 1.01 (t,j=7.1 Hz, 3H). M$^{+1}$=320.

c) N-(3-Amino-4-butoxy-5-iodobenzyl)-N-hydroxyformamide

5-Amino-4-butoxy-3-iodobenzaldehyde was converted to the title compound using the methods described in example 2d. $^1$H NMR (400 MHz, CDCl$_3$) δ 8.18* 7.94 (s, 1H), 7.13* 7.06 (s, 1H), 6.63 (s, 1H), 4.52* 4.47 (s, 2H) 3.90 (t, j=6.2 Hz, 2H), 1.82–1.86 (m, 2H), 1.54–1.59 (m, 2H), 1.02 (t, j=7.1 Hz, 3H). M$^{+1}$=365.

* peaks due to rotamer d) N-(4-Butoxy-3-iodo-5-methylaminobenzyl)-N-hydroxyformamide A mixture of N-(3-amino-4-butoxy-5-iodo-benzyl)-N-hydroxy-formamide (36 mg, 0.1 mmol), potassium carbonate (11 mg, 0.11 mmol) and iodomethane (9.2 ul, 0.15 mmol) in DMF (1 ml) was stirred 18 h at room temperature. The mixture was partitioned between ethyl acetate and water, the organic extract was washed with brine then dried with sodium sulfate and all voltiles removed. Purification by preparative HPLC afforded the title compound (8 mg, 22%) $^1$H NMR (400 MHz, CD$_3$OD) δ 8.36* 7.16 (s, 1H), 7.00 (s, 1H), 6.59 (s, 1H), 4.58* 4.54 (s, 2H) 3.84 (t, j=6.2 Hz, 2H), 2.83* 2.81 (s, 3H) 1.83–1.87 (m, 2H), 1.54–1.59 (m, 2H), 1.03 (t, j=7.1 Hz, 3H). M$^{+1}$=379.

EXAMPLE 7

Preparation of N-(4-butoxy-3-chloro-5-methoxybenzyl)-N-hydroxyformamide a) 4-Butoxy-3-chloro-5-methoxybenzaldehyde 4-Hydroxy-3-chloro-5-hydroxybenzaldehyde was converted to the title compound using the methods described in example 6a. $M^{+1}$=243.

b) N-(4-butoxy-3-chloro-5-methoxybenzyl)-N-hydroxyformamide

4-Butoxy-3-chloro-5-methoxybenzaldehyde was converted to the title compound using the methods described in example 2d. $^1$H NMR (400 MHz, $CD_3OD$) δ 8.49* 8.06 (s, 1H), 6.94* 6.91 (s, 1H), 6.73 (s, 1H), 4.64* 4.59 (s, 2H) 3.99 (t, j=6.2 Hz, 2H), 1.73–1.81 (m, 2H), 1.47–1.59 (m, 2H), 0.97 (t, j=7.3 Hz, 3H). $M^{+1}$=288.

With appropriate manipulation and protection of any chemical functionality, synthesis of the remaining compounds of Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

The present compounds are useful for the treatment of bacterial infections including but not limited to respiratory tract infections and/or Gram positive infections.

Compounds of Formula (I) and their pharmaceutically acceptable salts may be administered in a standard manner for antibiotics, for example orally, parenterally, sublingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of Formula (I) or a pharmaceutically acceptable salt thereof calculated as the free acid the daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following test:

Biological Assay:

*S. Aureus* or *E. Coli* PDF activity is measured at 25° C., using a continuous enzyme-linked assay developed by Lazennec & Meinnel, (1997) "Formate dehydrogenase-coupled spectrophotometric assay of peptide deformylase" Anal. Biochem. 244, pp. 180–182, with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def enzyme, and absorbance is monitored for 20 min at 340 nm.

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mg/ml. A panel of 12 strains were evaluated in the assay. This panel consisted of the following laboratory strains: *Staphylococcus aureus* Oxford, *Streptococcus pneumoniae* R6, *Streptococcus pyogenes* CN10, *Enterococcus faecalis* I, *Haemophilus influenzae* Q1, *Escherichia coli* DC0, *E. coli* EES, *E. coli* 7623 (AcrAB+) *E. coli* 120 (AcrAB-) *Klebsiella pneumoniae* E70, *Pseudomonas aeruginosa* K799 wt and *Candida albicans* GRI681. The minimum inhibitory concentration (MIC) was determined as the lowest concentration of compound that inhibited visible growth. A mirror reader was used to assist in determining the MIC endpoint.

All publications, including but not limited to patents and patent applications cited in this specification are herein incorporated by reference as if each individual publication were specifically and individually indicated to be incorporated by reference as though fully set forth.

What is claimed is:

1. A compound according to formula (I):

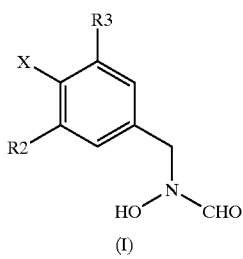

(I)

wherein:
X is selected from the group consisting of —C(O)OC$_{1-3}$ alkyl, —OR1, —NR1R6, —C(O)NR1R6, or —C(O)R6;

R1 is selected from the group consisting of hydrogen, C$_{1-6}$alkyl, unsubstituted or substituted by one or more moieties selected from the group consisting of alcohol, ether, amine, amide, carboxylic acid, lactam, Ar, —C$_{1-2}$ alkyl Ar, C$_{0-2}$alkylpiperidin-4-yl, substituted on nitrogen with R7, and C$_{0-2}$alkylpyrrolidin-3-yl, substituted on nitrogen with R7 or C$_{0-2}$ morpholine);

R6 is selected from the group consisting of hydrogen, C$_{1-6}$alkyl, unsubstituted or substituted by one or more moieties selected from the group consisting of halide, alcohol, ether, amine and amide;

or, R1 and R6 taken together may constitute a 5 or 6 member cyclic system which may contain an O or an optionally substituted N;

Ar is selected from the group consisting of phenyl, furyl, pyridyl, thienyl, thiazolyl, isothiazolyl, pyrazolyl, triazolyl, tetrazolyl, imidazolyl, benzofuranyl, indolyl, thiazolidinyl, isoxazolyl, oxadiazolyl, thiadiazolyl, pyrrolyl, and pyrimidyl, all of which may be unsubstituted or substituted by one or more R4 or R5 groups;

R2 is selected from the group consisting of I, Br, Cl, isopropyl and tert-butyl;

R3 is selected from the group consisting of H, I, Br, Cl, isopropyl, tert-butyl and Z-R8;

Z is selected from the group consisting of O, —NH, —NHC(O), —C(O)NH, —SO$_2$NH, —CONHSO$_2$, —CONHNHCO and —CH$_2$;

R4 and R5 are independently selected from the group consisting of hydrogen, —OR9, —CN, F, Cl, Br, I, —CO$_2$H, —C(O)NR1R6, —NR6COR6, —NH$_2$, and —C$_{1-4}$ alkyl which may be unsubstituted or substituted by one or more alcohol, amine, amide or carboxylic acid moieties;

R9 is H, —CH$_3$ or —CF3;

R7 is selected from the group consisting of hydrogen, —C$_{1-4}$acyl and —C$_{1-4}$alkoxycarbonyl;

R8 is selected from the group consisting of C$_{1-4}$alkyl which may be unsubstituted or substituted by one or more alcohol, amine, amide, carboxylic acid, aryl or carbocycle.

2. A compound according to claim 1 selected from the group consisting of:
N-Hydroxy-N-(4-methoxy-3,5-dimethylbenzyl) formamide;
N-(3,5-Diisopropyl-4-methoxybenzyl)-N-hydroxyformamide;
Methyl 2,6-dichloro-4-(N-formyl-N-hydroxyaminomethyl)benzoate;
N-[3,5-Dichlorobenzyl]-N-hydroxyformamide;
N-[3,5-Dichloro-4-methoxybenzyl]-N-hydroxyformamide;
N-Hydroxy-N-(4-amino-3,5-dichlorobenzyl)formamide;
N-[3,5-Dichloro-4-(2-thiophen-2-ylethoxy)benzyl]-N-hydroxyformamide;
N-[3,5-Dichloro-4-(2-hydroxyethoxy)benzyl]-N-hydroxyformamide;
N-[3,5-Dichloro-4-(pyridin-4-ylmethoxy)-benzyl]-N-hydroxy-formamide;
N-[3,5-Dichloro-4-((S)-1-methyl-2,5-dioxo-pyrrolidin-3-yloxy)-benzyl]-N-hydroxy-formamide;
2-Butoxy-3-chloro-N-(2,3-dihydroxypropyl)-5-[(formylhydroxyamino)methyl]-benzamide;
N-{3,5-Dichloro-4-[2-(2-oxo-pyrrolidin-1-yl)-ethoxy]-benzyl}-N-hydroxy-formamide;
2-Butoxy-3-chloro-5-[(formyl-hydroxy-amino)-methyl]-benzoic acid methyl ester;
N-[3,5-Dichloro-4-(1-ethyl-butoxy)-benzyl]-N-hydroxy-formamide;
N-hydroxy-N-(3-iodo-5-methoxy-4-phenoxy-benzyl)-formamide;
N-(4-butoxy-3-iodo-5-methoxy-benzyl)-N-hydroxy-formamide;
N-(4-cyclohexyloxy-3,5-dichloro-benzyl)-N-hydroxy-formamide;
N-(2-Acetylaminoethyl)-2-butoxy-3-chloro-5-[(formylhydroxyamino)methyl]benzamide;
N-(4-butoxyl-3-chloro-5-hydroxy-benzyl)-N-hydroxy-formamide;
N-hydroxy-N-[3-iodo-5-methoxy-4-(2-methoxy-ethoxy)-benzyl]-formamide;
N-[3-Chloro-4-(3,4-dichloro-phenoxy)-5-methoxybenzyl]-N-hydroxy-formamide;
N-[4-butoxy-2,3-dichloro-5-methoxy-benzyl]-N-hydroxy-formamide;
N-{2-Butoxy-5-[(formyl-hydroxy-amino)-methyl]-3-iodo-phenyl}-acetamide;
2-{2-Butoxy-5-[(formyl-hydroxy-amino)-methyl]-3-iodo-phenoxy}-N-methyl-acetamide and
N-(3-Chloro-5-methoxy-4-phenoxybenzyl)-N-hydroxyformamide.

3. A compound according to claim 1 selected from the group consisting of:
N-Hydroxy-N-[4-(4-hydroxyphenoxy)-3,5-diiodobenzyl] formamide;
N-[3,5-Dichloro-4-(4-methoxyphenoxy)benzyl]-N-hydroxyformamide;
N-(4-Butoxy-3,5-dichlorobenzyl)-N-hydroxyformamide;
N-(3-Chloro-5-methoxy-4-phenoxybenzyl)-N-hydroxyformamide;
N-(4-butoxy-3-chloro-5-methoxybenzyl)-N-hydroxyformamide;
2-{2-Butoxy-3-chloro-5-[(formylhydroxyamino)methyl] phenoxy}-N-methyl acetamide and
N-(4-Butoxy-3-iodo-5-methylamino-benzyl)-N-hydroxyformamide.

4. A method of treating a bacterial infection by administering to a subject in need of treatment a compound according to claim 1.

5. A method according to claim 4, wherein the compound is selected from the group consisting of:

N-Hydroxy-N-(4-methoxy-3,5-dimethylbenzyl)formamide;

N-(3,5-Diisopropyl-4-methoxybenzyl)-N-hydroxyformamide; Methyl 2,6-dichloro-4-(N-formyl-N-hydroxyaminomethyl)benzoate;

N-[3,5-Dichlorobenzyl]-N-hydroxyformamide;

N-[3,5-Dichloro-4-methoxybenzyl]-N-hydroxyformamide;

N-Hydroxy-N-(4-amino-3,5-dichlorobenzyl)formamide;

N-[3,5-Dichloro-4-(2-thiophen-2-ylethoxy)benzyl]-N-hydroxyformamide;

N-[3,5-Dichloro-4(2-hydroxyethoxy)benzyl]-N-hydroxyformamide and

N-(3-Chloro-5-methoxy-4-phenoxybenzyl)-N-hydroxyformamide.

6. A method of treating a bacterial infection according to claim 5 selected from the group consisting of respiratory tract infection, and Gram+TPP.

* * * * *